United States Patent [19]

Chen et al.

[11] Patent Number: 5,746,876
[45] Date of Patent: May 5, 1998

[54] SAFETY SAMPLER FOR HOT ACID IN SEMICONDUCTOR MANUFACTURING FAB

[75] Inventors: Shun-Long Chen; Kuo-Yue Hsu, both of Hsin-Chu, Taiwan

[73] Assignee: Taiwan Semiconductor Manufacturing Company, Ltd., Hsinchu, Taiwan

[21] Appl. No.: 657,232

[22] Filed: Jun. 3, 1996

[51] Int. Cl.⁶ ................................. H01L 21/00
[52] U.S. Cl. ............................ 156/345; 216/84
[58] Field of Search ............... 156/345 L, 345 LC, 156/345 LP; 216/84, 90, 91; 438/14, 745, 747

[56] References Cited

U.S. PATENT DOCUMENTS

| | | | |
|---|---|---|---|
| 3,959,046 | 5/1976 | Bussmann et al. | 216/84 X |
| 4,448,635 | 5/1984 | Kuiken et al. | 216/90 |
| 4,501,636 | 2/1985 | Valley | 156/345 |
| 4,578,137 | 3/1986 | Kring | 156/345 |
| 5,236,750 | 8/1993 | Duret et al. | 428/35.7 |
| 5,325,730 | 7/1994 | Wang | 438/14 X |

*Primary Examiner*—William Powell
*Attorney, Agent, or Firm*—George O. Saile; Stephen B. Ackerman

[57] ABSTRACT

A chemical apparatus is proposed where sampling of hazardous materials in semiconductor fabs, or manufacturing lines, is made easier and more productive. A sampler cup is provided which has a spout and a relatively long handle which in turn is equipped with a round shield fitted close to its end. The shield is used to protect the operator from the chemical effects and heat of the sampled substance. The cup is then placed into a second container, or a beaker, which has formed on its open edge notches where the long handle of the cup can be placed with ease. As a further means for secure placement, the cup has a recess at the bottom surface on the outside such that it captures a pedestal that is formed at the bottom of the beaker on the inside. Furthermore, the beaker has a handle which is protected by a still another protective sleeve formed in cylindrical shape around the handle. In this manner, the cup is held in one hand, while the beaker in the other, and the hazardous material is transported readily. It is shown that where such apparatus is not available in prior art, as much as four hours per day can be saved in a manufacturing line, because with the disclosed apparatus, hot sampling can be done without having to shut down the line and wait for the process tank to cool down.

41 Claims, 4 Drawing Sheets

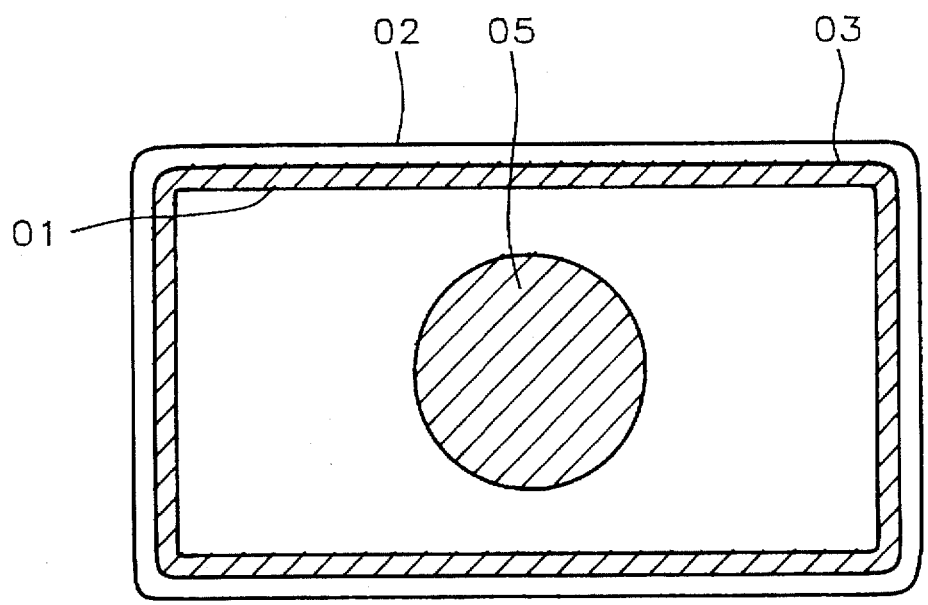
FIG. 1a - Prior Art
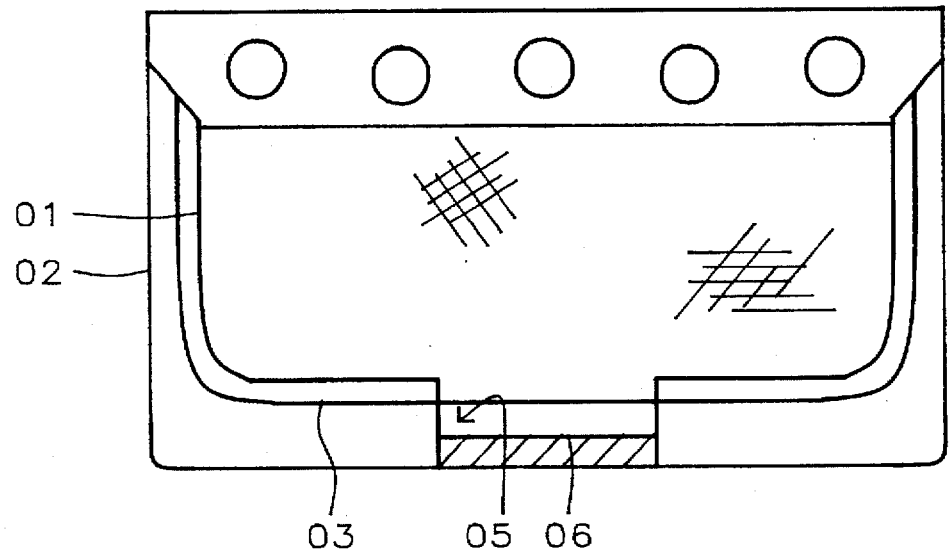
FIG. 1b - Prior Art

SAFETY SAMPLER FOR HOT ACID IN SEMICONDUCTOR MANUFACTURING FAB

BACKGROUND OF THE INVENTION

(1) Field of the Invention

The invention relates generally to handling hazardous materials and more particularly to apparatus employing safety features in sampling hot acid solutions in the manufacturing environment of a semiconductor fabricator or fab.

(2) Description of the Related Art

One of the key aspects of a manufacturing line in a fab is the large number of wet processing steps that a semiconductor substrate must be subjected to in fabricating integrated circuit devices. Some of the wet processes include wafer cleaning, wet etching, and photoresist removal. The chemical baths that are used in each one of these processes must be prepared with appropriate solutions and be kept at specified temperatures. Wet etching of silicon dioxide in wafers for example, is usually accomplished with various hydrofluoric acid (HF) solutions. Silicon nitride ($Si_3N_4$) is etched by reflux boiling of phosphoric acid at 180° C. similarly, the etching of aluminum and aluminum alloys is generally done in heated solutions of phosphoric acid, nitric acid, acetic acid, and water. Some other processes employ the highly corrosive sulfuric acid, which is usually heated to a temperature on the order of about 150° C. For example, sulfuric peroxide mixture which is used for removing photoresist can form the corrosive $HO-O-SO_2-OH$ acid. Phosphoric acid used for removing silicon—nitride, $Si_3N_4$ is can be as hot as 180° C.

The chemical solutions in each one of these hot baths must be checked and tested at certain intervals of time to make sure that the pH and concentration levels are according to a set of specifications. The place where the tests are conducted is usually at different locations than where the baths are found. Large etching baths are kept in floor-tanks, while the smaller baths are kept in glass beakers under hooded (ventilated cover) bench-tops. When testing is required, personnel on the manufacturing floor would shut down the operations at a tank, and wait until the solution cooled down. Sometimes, the waiting time could be as long as four hours. After it has cooled down sufficiently, the operator would scoop up a sample of the solution and carry it to a test station where the testing would be done.

It will be appreciated that such down-time cannot be tolerated in today's competitive market place. The number of wet processing steps that are involved in a semiconductor manufacturing line are many as stated before and, therefore, the total amount of down-time can readily become prohibitive. It will be seen in the present invention that chemical apparatus with suitable provisions can make it possible to approach and retrieve samples from process tanks that hold hazardous substances without the need for actually stopping the process taking place in the tank. In this manner, any time lost due to process sampling is eliminated.

The apparatus that is proposed and described in this invention is equipped with shields and handles that protect the operator from detrimental effects of the hazardous materials. Furthermore, the part of the apparatus that is most vulnerable to a mishap is protected inside another apparatus, especially when in transit. Provisions are made in the design of the apparatus for the operator to choose a combination of positions that is suitably most safe for him or her to carry samples from one location to another in a manufacturing line.

Prior art, on the other hand, does not allow the handling of hot chemicals in transport by humans in a semiconductor manufacturing fab, though there are bath apparatus that are designed to house hazardous materials. One such apparatus described in U.S. Pat. No. 4,578,137 is a beaker with a heater wrapped around its outer walls and placed inside another vessel such that the heater is protected from fumes and chemical splash or spillage. For example, in the plan view of FIG. 1a of prior art, a beaker (01) with no top lid is shown placed in a quartz jar (02). In this particular case, the beaker (01) is fitted with a heater (03) and holes (04) are provided both around the upper edge and also around the outside walls of the jar to keep the temperature uniform.

To aid further in the uniformity of the temperature of the liquid in the beaker, the bottom of the beaker is shaped in the manner shown (05) in FIG. 1b to accept a magnetic stirrer (not shown) in it. The lower portion (05) of the beaker is then placed on top of a resilient pedestal (06) at the bottom of jar (02). However, neither one of the two vessels is equipped with a handle for transport from one place to another. Furthermore, the entire weight of the beaker and the solution contained therein can exceed 50 pounds, placing a substantial burden on the person(s) carrying it. In yet another disclosure made in U.S. Pat. No. 5,236,750, an apparatus is described with a metal wall coated with a protective material and is intended to contain hydrofluoric acid. However, the apparatus is not suitable to be carried easily and naturally.

Thus, in addition to the down-time in waiting for the chemical solutions to cool before they can be carried with conventional apparatus, health and safety issues are important considerations during handling of the apparatus in a manufacturing environment. It is, therefore, evident that there is a need for a container which is suitable for taking hot solution samples from chemical baths and transporting them safely from one place to another.

SUMMARY OF THE INVENTION

It is therefore an object of this invention to provide a chemical apparatus which is formed to be suitable for transporting hot liquids in a semiconductor manufacturing line.

It is another object of this invention to provide a chemical apparatus which enables the operation of a manufacturing sector without being shut down.

It is a further object of the present invention to provide a chemical apparatus with safety features for human operators.

These objects are achieved by providing a sampler container which can be placed inside a second supporter container. The sampler container has a spout and a relatively long handle which in turn is equipped with a round shield fitted close to its end. Said first container is used to retrieve samples of hot liquids from chemical baths. The supporter container also has a handle, but is rectangularly shaped and affixed to said container spanwise of the whole height of the container. Surrounding the rectangular handle of the second container is yet another cylindrical shield large enough to accommodate a hand and wrist of a person. The second container is notched at one or more places around the rim so that while it is being held with one hand, the long handle of the sampler in the other hand may be placed in one of the notches in the most comfortable position as the sampler is lowered into the supporter container. A round pedestal is formed at the bottom of the supporter container such that a mating circular recess that is formed at the bottom of the sampler will accept the pedestal when the sampler is set inside said second supporter container.

BRIEF DESCRIPTION OF THE DRAWINGS

FIG. 1a is a top view of a prior art chemical apparatus where a container with a heater around it is placed inside another container.

FIG. 1b is a side view of the prior art chemical apparatus shown in FIG. 1b.

Figure 2A:
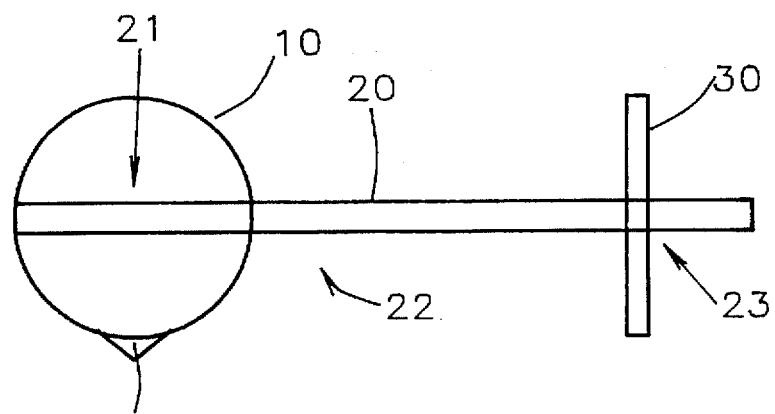
FIG. 2a is a top view of a sampler cup of the present invention.

The drawings are not necessarily drawn to scale, but instead are drawn so as to illustrate the important features of the invention.

DESCRIPTION OF THE PREFERRED EMBODIMENTS

Referring now to the drawings, more particularly to FIGS. 2a–2c, and FIGS. 3a–3c, there is illustrated a set of chemical bath apparatus embodying the elements for improving the handling of hot and hazardous liquids in a semiconductor manufacturing line, or fab.

In order best to understand the spirit of the invention in its entirety, the key features of the apparatus will be described first in terms of their function and workings together. The preferred embodiments will be understood more readily thereafter.

One of the apparatus of the present invention shown in FIG. 2a is a cup (10), preferably consisting of quartz glass, as is common in prior art. The cup is a sampler container used for the purposes of retrieving samples of hot process liquids from chemical baths. The hot liquid is usually scooped up from tanks or poured from other containers that hold chemical baths where the temperatures are in between about 120° C. to 180° C. In prior art, lacking proper apparatus, it is not usually safe to retrieve such hot liquids without interrupting the process taking place in the chemical baths, and letting the liquid cool down first. The cup (10) of the present invention has a multiplicity of safety features, namely a long handle (20) which in turn is equipped with a translucent shield (30). It has been determined through experimentation and experience in the manufacturing line that said handle preferably have a length in between about 190 mm to 210 mm from the side of the cup (10) up to the shield (30), namely the region (22) in FIG. 2a. The portion of the handle projecting outwards from the shield (30), namely, region (23), is formed in between about 90 to 110 mm long to accommodate comfortably the hand and glove of an operator. The handle is a quartz bar with a diameter (24) in between about 10 to 12 mm, and continuously spans the opening of the cup in region (21).

The safety features described above are designed to protect the operator from both the intense heat of the sample liquids, and the chemical effects of the same. A splash or spillage of hydrochloric or sulfuric acid, for example, cannot be tolerated as is common knowledge. Therefore, the position of the shield and its size must be such as to minimize the radiation of heat emanating from the liquid in the cup to the body of the operator holding the cup, as well as minimizing the possibility of a splash landing on the operator. For these reasons, the preferred diameter of the shield is between about 135 mm to 140 mm. It is also noted that the shield is mounted on the handle asymmetrically; that is, the top portion of the shield protrudes about one-third of its diameter above the handle and the two-thirds, below it. Laterally, the center of the handle bar is aligned with the vertical diameter of the shield. In this manner, the bottom portion of the shield can protect the lower part of the head and neck of the operator, while the upper part may be quickly moved upwards to protect the eyes. The operator never looses sight of the cup itself, as it should be, since the shield is made out of translucent material, preferably, quartz glass. In another embodiment, the shield is made in an elliptical shape where the handle bar is affixed in a hole formed at one of the two foci of the ellipse.

Figure 2B:
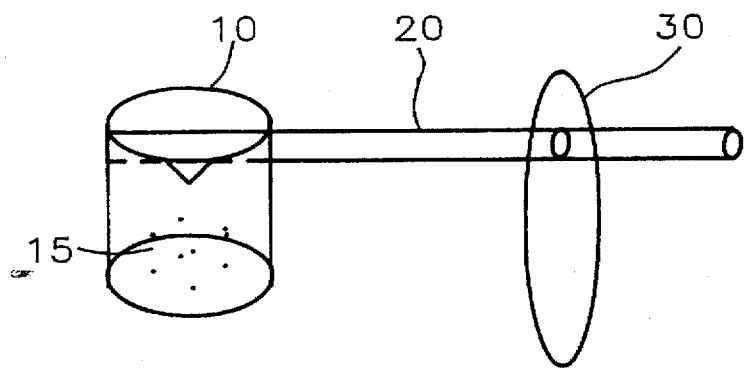
FIG. 2b is a perspective drawing of the sampler cup of FIG. 2a, where a handle and a shield are also shown according to the present invention.
Figure 2C:
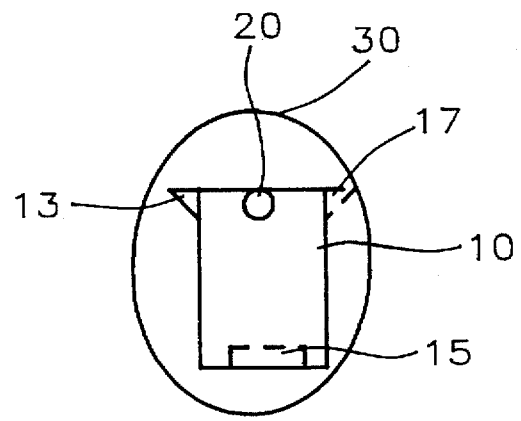
FIG. 2c is a side view of the cup of the present invention.

The weight of the apparatus becomes important when transporting hazardous materials from one place to another in the manufacturing line. For this reason, the size of the cup and thickness of the materials are also carefully taken into account to provide a relatively light load to carry on the part of the operator. Furthermore, the moment of the weight of the cup, along with its contents, with respect to the moment arm extending to the end of the handle where it is being held is also considered in this invention to provide a most suitable apparatus for transporting liquids without undue tilting or jostling while in motion. Thus, the diameter of the sampler cup is between about 65 mm to 70 mm and the wall-thickness is between about 2.5 mm to 3.5 mm) while the height is between about 85 mm to 95 mm to yield a volume between about 200 milliliters (ml) to 250 ml, that is, approximately a 250 ml container. Good stability is also required while pouring out the contents of the cup. For this purpose, a spout (13) is provided, however, in a particular orientation in relation to the handle. As shown in FIG. 2b, the preferred placement of the spout is between about 87° to 93° with respect to the handle (20). Whether said angle is plus or minus, that is whether to one side or the opposite side of the cup in relation to the handle does not matter excepting perhaps the preferences of right-handed or left-handed persons. It another embodiment, a plurality of spouts, such as the phantom one (17) shown in side view FIG. 2c, are placed on the cup so as to provide a wider range of use by different operators.

Figure 3A:
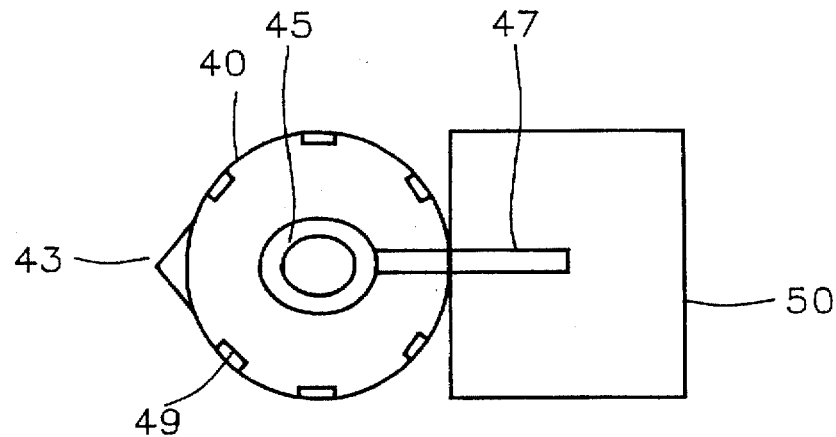
FIG. 3a is a top view of a supporter beaker of the present invention.
Figure 3B:
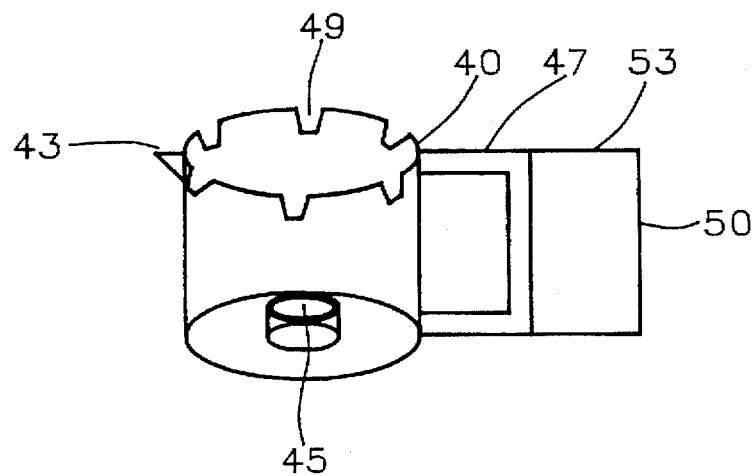
FIG. 3b is a perspective drawing of the supporter beaker of FIG. 3a, where a handle and a shield are also shown according to the present invention.

A second apparatus of the present invention is shown in FIG. 3a, and is comprised of a supporter container, or beaker, (40), a spout (43), a handle (47) and a hand protector sleeve (50). The supporter container is designed to accept the sampler container as will be described more in detail later. The diameter of said supporter container is between about 90 mm to 95 mm and the wall-thickness is between about 2.5 mm to 3.5 mm while the height is between about 115 mm to 125 mm to yield a volume between about 400 milliliters (ml) to 500 ml, that is, approximately a 500 ml container. Being a support container, beaker (40) is formed with a handle that is rectangularly shaped (47) as shown in FIG. 3b, and affixed to said container spanwise the whole height of the container specified before so that the beaker can be held strongly by one hand while the hand in glove, usually, can wrap around the handle with a assured support from the handle. The handle is formed of quartz of diameter between about 7 mm to 8 mm, and is 50 mm long in region (51) of FIG. 3b. Furthermore, the hand holding the beaker (40) in support of the cup (10) that is placed inside it must be protected from the heat and corrosive effects of the sample substance that is being carried inside the cup. For this purpose, a sleeve (50) is formed in the form of a cylinder around said rectangular handle such that it can accommodate a hand and a wrist of a person. The outside diameter of the sleeve shield is between about 118 mm and 122 mm with a wall-thickness of between about 2.5 mm to 3.5 mm and consists of quartz glass. It will be appreciated that the sleeve so formed must be of sufficient length that while being able to accommodate a hand and a wrist, it must also allow the wrist to bend so that the desired leverage and strength can be achieved comfortably by the person holding and transporting the cup-beaker combination. The preferred length of said sleeve is between about 100 mm to 120 mm.)

Spout (43) of said beaker (40) as shown in the top view of FIG. 3a and the perspective view of FIG. 3b is aligned differently with respect to the handle (47) of the beaker than the spout (13) of cup (10) with respect to its handle (20). A spout is provided for the beaker in the first place as a means to pour any substance that may spill out of the cup as or when the latter is being placed inside the beaker, or when the contents of the cup are poured into still another container while the cup is still being held inside the beaker. Said spout (43) is on the opposite side of said handle (47) of said beaker (40).

Other positions on the edge of said beaker (40) are formed with a plurality of notches (49) as shown in FIGS. 3a and 3b. Said notches serve as support places for handle (20) of sampler cup (10) of FIG. 2b. It will be appreciated that when cup (10) is lowered into the support beaker (40), handle (20) must be placed on the edge of beaker (40). However, since said beaker (40) consists of quartz glass, which is usually a relatively frictionless and smooth surface, the edge of the beaker must be provided by a means by which handle (20) can be secured positively thereon or therein. Said notches (49), therefore, are of about the dimensions of said handle (20) and reasonably tapered to provide said means. In addition, said notches are preferably formed at 45° intervals starting at handle (47), excepting, of course, where the handle itself is located, and at 180°, that is, at the opposite side to the handle where spout (43) is located.

The ease with which the sampler cup (10) is placed into supporter beaker (40) is accomplished by positioning the handle (20) of said cup into any one of plurality of notches (49) on the edge of the supporter beaker (40). It will be appreciated that the positioning of said handle into a notch is a function of several variables including the physique of the operator, the weight of the sampler cup and how the supporter beaker is being held by the other hand manipulating it. Thus, in FIG. 4a, the operator is holding the cup (10) at right angles to the supporter beaker (40). He can now transport the sample liquid to a test station or other parts of the manufacturing line thereof at his own gait without a danger of spilling or splashing the liquid outside of the supporter beaker. The operator of FIG. 4b, on the other hand, prefers to place the handle (20) at a 45° angle into notches (49) of supporter beaker (40). Said notches, therefore, enable the operator to be able to choose carrying positions that are suitable to him or her, which is an improvement over prior art methods.

Figure 3C:
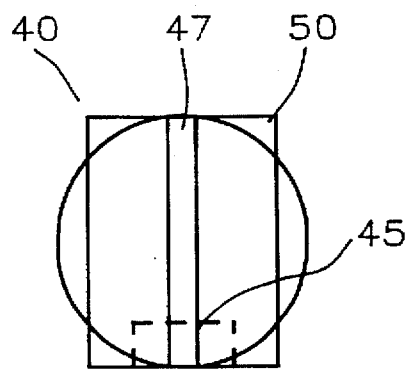
FIG. 3c is a side view of the beaker of the present invention..
Figure 4A:
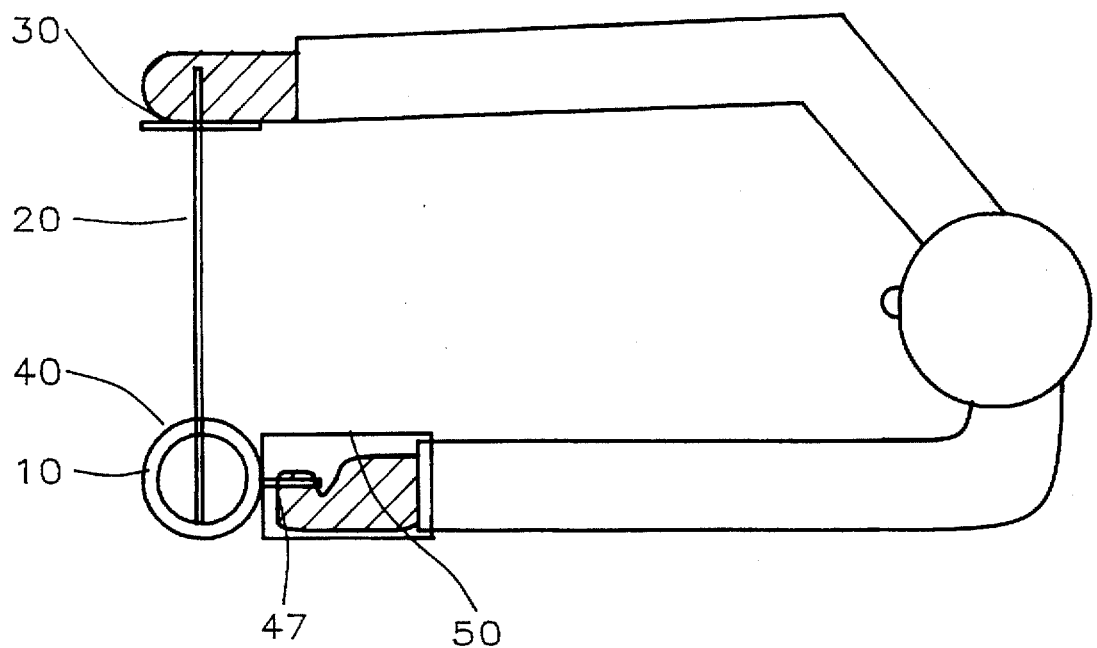
FIG. 4a shows a mode of handling of the sampler cup and its supporter beaker according to this invention.
Figure 4B:
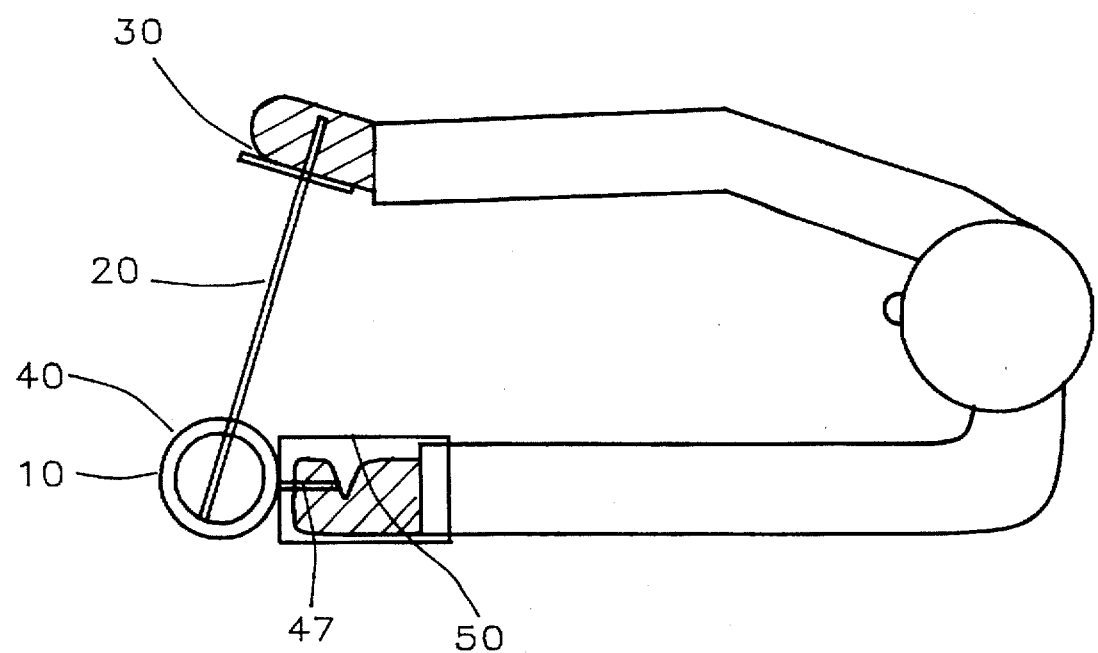
FIG. 4b shows another mode of handling of the sampler cup and its supporter beaker according to this invention.

While it would be possible to transport the sampler cup (10) of FIG. 4a in its support beaker (40) of the same figure in the manner described so far, a further improvement is disclosed whereby the cup is more positively secured into the beaker. This is accomplished by providing a round pedestal (45) as shown in FIG. 3b, which fits into a circular mating recess (15) formed at the bottom of sampler cup (10) in FIG. 2b. Side views of both said recess (15) and said pedestal (45) are also shown in FIGS. 2c, and 3c, respectively. The pedestal engages into the recess as the sampler cup is lowered into the supporter beaker. It will be observed that while the previously described handle (20) resting in notch (49) provides angular stability for the cup, the engagement of pedestal (45) into recess (15) provides lateral stability during the transport of sampler cup (10) in its supporter beaker (40)

The pedestal can be formed of any shape, such as a cross, star, triangular, rectangular, and so on without departing from the spirit of the invention. However, a ring shaped pedestal with an outside diameter between about 45 mm to 55 mm, a thickness between about 8 mm to 10 mm and a height between about 8 mm to 12 mm is preferred. The recess (15) fits over the pedestal (45) with a tolerance between about 2 mm to 3 mm.

While the invention has been particularly shown and described with reference to the preferred embodiments thereof, it will be understood by those skilled in the art that various changes in form and details may be made without departing from the spirit and scope of the invention.

What is claimed is:

1. An apparatus for transporting substances to be processed in a manufacturing line comprising:
    a container for storing said substances;
    said container having a handle;
    said container having a shield;
    said container having a plurality of spouts; and
    said container having a recessed bottom.

2. The apparatus of claim 1, wherein said container is a sampler cup and consists of quartz glass.

3. The apparatus of claim 2, wherein said cup has a diameter between about 65 mm to 70 mm.

4. The apparatus of claim 2, wherein said cup has a wall-thickness between about 2.5 mm to 3.5 mm.

5. The apparatus of claim 2, wherein said cup has a height between about 85 mm to 95 mm.

6. The apparatus of claim 1, wherein said handle consists of quartz glass rod.

7. The apparatus of claim 1, wherein said handle has a length of between about 190 mm to 210 mm.

8. The apparatus of claim 1, wherein said handle has a diameter of between about 190 mm to 210 mm.

9. The apparatus of claim 1, wherein said shield consists of quartz glass.

10. The apparatus of claim 1, wherein said shield is of circular shape and has a diameter between about 135 mm to 140 mm.

11. The apparatus of claim 1, wherein said shield has a thickness between about 3 mm and 4 mm.

12. The apparatus of claim 1, wherein said shield is affixed perpendicularly to said handle at one-third of its vertical diameter axis.

13. The apparatus of claim 1, wherein said spout is placed at an angle between about 87° to 93° with respect to said handle.

14. The apparatus of claim 1, wherein said plurality of spouts is placed at an angle between about 87° to 93° with respect to either or both sides of said handle.

15. The apparatus of claim 1, wherein said recessed bottom has a diameter between about 47 mm to 57 mm.

16. The apparatus of claim 1, wherein said recessed bottom has a depth of between about 9 mm to 13 mm.

17. An apparatus for transporting substances to be processed in a manufacturing line comprising:
    a container for protecting another container;

a container having notches;

said container having a handle;

said container having a sleeve;

said container having a spout; and said container having a pedestal.

18. The apparatus of claim 17, wherein said container is a supporter beaker and consists of quartz glass.

19. The apparatus of claim 18, wherein said beaker has a diameter between about 90 mm to 95 mm.

20. The apparatus of claim 18, wherein said beaker has a wall-thickness between about 2.5 mm to 3.5 mm.

21. The apparatus of claim 18, wherein said beaker has a height between about 115 mm to 125 mm.

22. The apparatus of claim 17, wherein said notches are formed on the edge of said beaker.

23. The apparatus of claim 17, wherein said notches are formed in between about 40° to 50° angle intervals around said edge of said beaker.

24. The apparatus of claim 17, wherein said handle consists of quartz glass rod.

25. The apparatus of claim 17, wherein said handle has a diameter of between about 7 mm to 8 mm.

26. The apparatus of claim 17, wherein said handle is of rectangular shape.

27. The apparatus of claim 24, wherein said rectangle has the dimensions of between about 50 mm×115 mm to 55 mm×125 mm.

28. The apparatus of claim 17, wherein said sleeve consists of quartz glass.

29. The apparatus of claim 17, wherein said sleeve is of cylindrical shape.

30. The apparatus of claim 17, wherein said sleeve has an outside diameter between about 118 mm to 122 mm.

31. The apparatus of claim 17, wherein said sleeve has a wall thickness between about 2.5 mm to 3.5 mm.

32. The apparatus of claim 17, wherein said sleeve has a length in between about 100 mm to 120 mm.

33. The apparatus of claim 17, wherein said spout is placed on the side opposite to and in line with said handle.

34. The apparatus of claim 17, wherein said pedestal consists of quartz glass.

35. The apparatus of claim 17, wherein said pedestal has an outside diameter between about 45 mm to 55 mm.

36. The apparatus of claim 17, wherein said pedestal has a thickness between about 8 mm to 10 mm.

37. The apparatus of claim 17, wherein said pedestal has a height between about 45 mm to 55 mm.

38. A combination apparatus for transporting substances to be processed in a manufacturing line comprising:

a cup having a straight handle and a protective shield for sampling said substances;

said cup having a recessed bottom on the outside;

said cup having spouts;

a beaker having a rectangular handle and a protective sleeve;

said beaker having notches; and said beaker having a bottom pedestal on the inside.

39. The apparatus of claim 38, wherein said straight handle of said cup fits in said notches of said beaker.

40. The apparatus of claim 39, wherein said notches are formed at angular intervals of in between about 40° to 50° in relation from said rectangular handle of said beaker.

41. The apparatus of claim 38, wherein said recessed bottom of said cup fits over said pedestal of said beaker.

* * * * *